US00PP15765P3

(12) United States Plant Patent
Kogawa

(10) Patent No.: US PP15,765 P3
(45) Date of Patent: May 17, 2005

(54) ***SKIMMIA JAPONICA* NAMED 'RANSO EN'**

(50) Latin Name: *Skimmia japonica*
Varietal Denomination: Ranso En

(75) Inventor: Noriaki Kogawa, Minia Tsukuda (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/278,606

(22) Filed: Oct. 22, 2002

(65) Prior Publication Data

US 2004/0078857 P1 Apr. 22, 2004

(51) Int. Cl.[7] ..... A01H 5/00
(52) U.S. Cl. ..... Plt./226
(58) Field of Search ..... Plt./226

*Primary Examiner*—Anne Marie Grunberg
(74) *Attorney, Agent, or Firm*—Christie, Parker & Hale, LLP

(57) ABSTRACT

A new plant variety of *Skimmia japonica* characterized Cream variegated margins.

1 Drawing Sheet

BACKGROUND OF THE INVENTION

Figure 1:
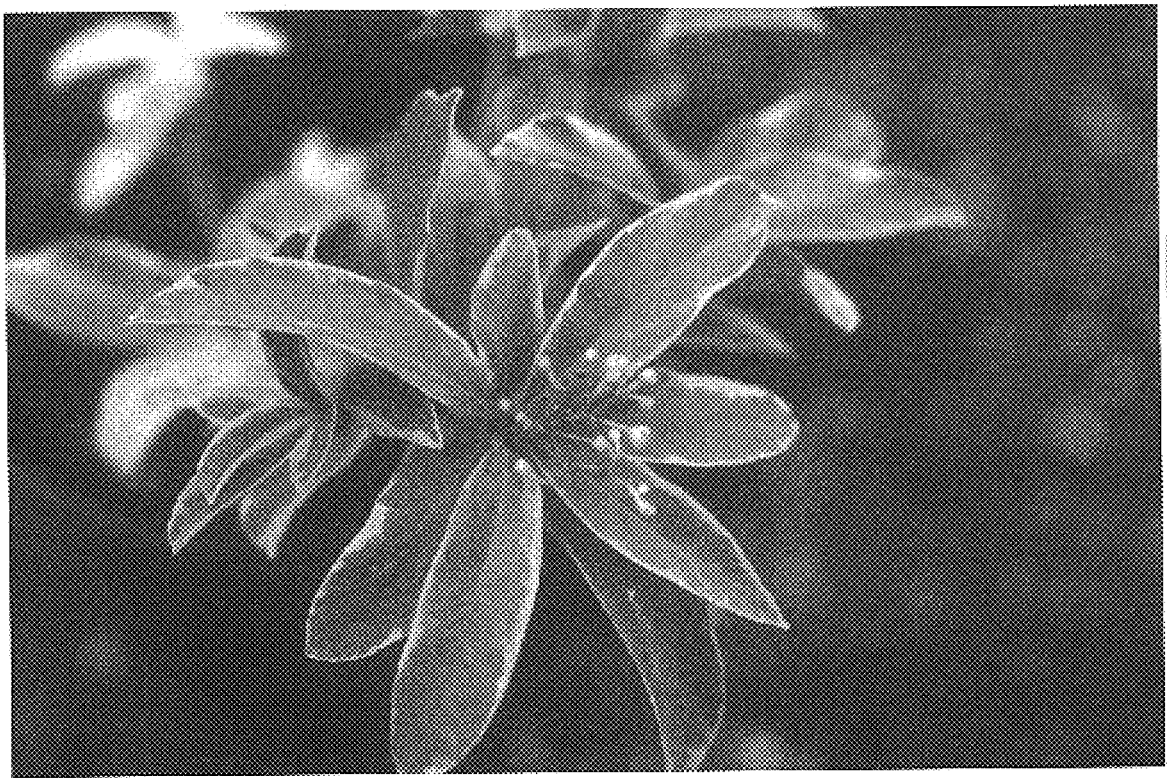

The present invention relates to a new and distinct variety of *Skimmia japonica,* which was found as a branch sport on a cultivated specimen of *Skimmia japonica* (unpatented) by Mr. Noriaki Kogawa in Minai Tsukuda, Aomori Prefecture, Japan. The varietal denomination of the new variety is 'Ranso En'.

The genus *Skimmia* is included in the family Ructaceae which comprises about 161 genera and 1700 species of evergreen and deciduous trees and shrubs, Asian in origin. *Skimmia* comprises approximately 6 species, orginating in Western Himalayas, Eastern China and Japan, many of which possess desirable ornamental characteristics. *Skimmia japonica* is a native of Japan and Korea.

SUMMARY OF THE INVENTION

The new variety was discovered as a branch sport and differs from its parent by having cream colored variegated margins. Asexual reproduction of the new variety by cuttings, performed in Vacaville, Calif., have confirmed that the distinctive characteristics of the new variety are stable and transmitted to succeeding generations, and the new variety reproduces true to type.

COMPARISON WITH PARENTS

'Ranso En' is distinguished from its parent and all other varieties of *Skimmia japonica* of which I am aware by having cream variegated margins.

BRIEF DESCRIPTION OF ILLUSTRATION

The accompanying illustrations shows a specimen of the new cultivar in a photo illustration as true to color as is reasonably possible to make in an illustration of this character.

FIG. 1 illustrates the distinctive cream colored marginal variegation.

DESCRIPTION OF THE NEW VARIETY

'Ranso En' has not been observed under all possible environmental, cultural and light conditions. The following observations and descriptions are of plants grown in Lewisberry, Pa. and Vacaville, Calif. In this description, color references are to The Royal Horticultural Society Colour Chart (2001) and terminology used in the color descriptions herein refers to plate numbers in this color chart. Phenotypic expression may vary with light intensity, cultural and environmental conditions.

Botanical classification: *Skimmia japonica* Thunb. 'Ranso En'.

*Parentage.*—Branch sport of *Skimmia japonica* (unpatented).

*Propagation.*—Vegetative cuttings.

Plant:

*Size.*—Between 50–60 cms tall.

*Habit.*—Evergreen shrub, upright to obliquely ascending, to spreading for older plants.

Branching:

*Lateral branches.*—Upright to obliquely ascending, to spreading on older plants.

*Typical branch quality.*—200.

*Observed branch quality.*—10.

*Size.*—50 to 60 cm long.

*Diameter.*—6 mm.

Color:

*Basal branches.*—Near Greyed Group 194C.

*Apical branches.*—Near Green Group 143C.

*Color of new shoots.*—Near Green Group 143C.

Leaf:

*Shape.*—Lanceolate to oblanceolate.

*Leaf size.*—Length 6.5 cm; width 2.5 cm.

*Arrangement.*—Alternate, simple.

*Margin.*—Smooth, entire.

*Texture/substance.*—Coriaceus, glabrous with a waxy surface covered with punctate glands.

Color: The following color readings are of specimens grown in Vacaville, Calif., and are of a 3 year old plant grown in a 2 quart container.

*New foliage.*—Upper side Center: Near Greyed-Green Group 191B. Upper side Margin: Near White Group 155B. Under side Center: Near Greyed-Green Group 191B. Under side Margin: Near White Group 155B.

*Mature foliage.*—Upper side Center: Near Greyed-Green Group 191B. Upper side Margin: Near White Group 155B. Under side Center: Near Greyed-Green Group 191B. Under side Margin: Near White Group 155B.

*Venation pattern.*—Upper Surface: Alternately pinnate, center vein depressed above. Under Surface: Side veins obscure, center vein raised beneath.

*Petioles.*—Size: 3 to 4 mm. Color: Near Greyed-Green Group 191B. Texture: Smooth. Internodes: 2 to 3 cm. Hardiness: USDA Zone 6 (−10° F. to 0° F.). Vigor: Slow to establish; moderate growth rate once established. Pests/Diseases: None Noted.

Infloresence:

*Bloom period.*—Outdoors: March. Greenhouse: Not observed in a greenhouse environment. Inflorescense Form: Cymes. Arrangement: Panicles to 5 cm long, unisexual; 4-merous. Sex of Flowers: All pistilate. Inflorescence Size: 4 to 8 cm. Shape of Inflorescence: Ovoid. Fragrance: Spicy.

*Lastingness of individual.*—Blooms: 2 to 3 weeks.

*Petals.*—Number/Arrangement: 4-merous. Shape: Narrowly oblong. Size: 4–5 mm long. Margin: Smooth, entire.

*Color.*—Upper surface: Near White Group N155B. Lower surface: Near White Group N155B.

*Sepals.*—Quantity: 4. Shape: Broadly triangular. Size: 1 to 2 mm. Margin: Finely ciliate. Color: Near White Group N155B.

*Peduncles.*—Length: Up to 8 cm. Diameter: 2 mm. Angle: 45 degrees. Color: Near Greyed-Green Group 191B.

*Buds.*—Rate of Opening: Moderate. Shape: Globose. Length: Less than 1 mm. Diameter: Less than 1 mm. Color: Near Red-Purple Group 62A.

*Gynocium.*—Stigma Appearance: Capitate, 4-parted. Style Size: 8 mm long. Seed Production: Drupes, globose, fleshy.

I claim:

1. A new variety of *Skimmia japonica* plant substantially as described and illustrated.

* * * * *